US006544170B1

(12) United States Patent
Kajihara et al.

(10) Patent No.: US 6,544,170 B1
(45) Date of Patent: Apr. 8, 2003

(54) BIOSIGNAL MEASURING METHOD AND APPARATUS

(75) Inventors: Shigeki Kajihara, Kyoto (JP); Shunichi Amari, Saitama (JP); Shiro Ikeda, Saitama (JP); Keisuke Toyama, Kyoto (JP)

(73) Assignees: Shimadzu Corporation, Kyoto (JP); Riken, Saitama (JP)

( * ) Notice: Subject to any disclaimer, the term of this patent is extended or adjusted under 35 U.S.C. 154(b) by 93 days.

(21) Appl. No.: 09/597,538

(22) Filed: Jun. 19, 2000

(30) Foreign Application Priority Data

Jun. 21, 1999 (JP) ..................... 11-173839 (P)

(51) Int. Cl.$^7$ ................................. A61B 5/00
(52) U.S. Cl. ....................... 600/300; 600/544
(58) Field of Search ................... 600/300, 301, 600/544, 545, 409, 408, 407; 128/897–925; 324/244–263; 327/510, 551

(56) References Cited

U.S. PATENT DOCUMENTS 4,736,751 A  *  4/1988 Gevins et al. ............. 600/544
5,601,081 A         2/1997 Tomita et al.

OTHER PUBLICATIONS

Gupta et al, Nonlinear Alignment and Averaging for Estimating the Evoked Potential, Apr. 1996, IEEE Transactions on Biomedical Engineering, vol. 13, No. 4, pp. 348–356.*
Makeig et al, Indendent Component Analysis of Electroencephalographic Data, Jun. 1, 1996, MIT Press, Advance in Neural Information Processing Conference, p. 145–51.*
Wang et al, Blind Separation of Multichannel Electrogastrograms Using Independent Component Analysis Based on a Neural Network, Jan. 1999, Medical & Biological Engineering & Computing, vol. 37, p. 80–86.*
Peterson et al, EEG–based Cognitive Task Classification with ICA and Neural Networks, Jun. 1, 1999, Springer–Verlag, Berlin Germany, Engineering Applications of Bio–Inspired Artificial Neural Networks International Work–Conference, p. 265–72.*

Patent Abstracts of Japan, "Biological Activity Current Source Estimating Device", Published Dec. 19, 1995; Inventor: Kajiwara Shigeki.

* cited by examiner

Primary Examiner—Eric F. Winakur
Assistant Examiner—David J. McCrosky
(74) Attorney, Agent, or Firm—Rader, Fishman & Grauer PLLC (57) ABSTRACT

A biosignal measuring apparatus for measuring, with a plurality of sensors, minute biosignals generated from bioelectric current sources in a region of a patient to be diagnosed. The apparatus includes a signal decomposer for decomposing detection signals provided by the plurality of sensors into a plurality of independent components, a noise component remover for determining noise components among the independent components based only on states of the independent components, and removing the noise components, a signal restorer for deriving restored detection signals from respective non-noise independent components, and a signal analyzer for determining an intracerebral activity corresponding to each independent component of each of the restored detection signals. After removing independent components determined to be noise components by the independent component analysis technique, a detection signal is separately restored for each information source from the remaining non-noise independent components. Thus, without requiring separate magnetic sensors exclusively for detecting noise, restored magnetism detection signals sufficiently stripped of noise components for the purpose of biosignal analysis are obtained with ease only from the signals acquired with biosignal measuring sensors.

35 Claims, 7 Drawing Sheets

Fig.8 ures and waveforms of the sensors are installed in different positions, and therefore the noise

BIOSIGNAL MEASURING METHOD AND APPARATUS

BACKGROUND OF THE INVENTION

1. Field of the Invention

This invention relates to a biosignal measuring method and apparatus using a magnetoencephalograph or electroencephalograph. More particularly, the invention relates to a technique for deducing intracerebral activity by removing noise components from detection signals acquired through biosignal measuring sensors.

2. Description of the Related Art

A living body produces minute biomagnetism (biological magnetic fields) as a result of bioelectric currents flowing in the living body. For example, the biomagnetism generated in the brain is called magnetoencephalo which includes induced magnetoencephalo formed by a stimulus applied to the living body, and spontaneous magnetoencephalo produced spontaneously such as alpha wave or spike wave associated with epilepsy.

In recent years, a multichannel SQUID sensor has been developed which uses SQUIDs (Superconducting Quantum Interference Devices) as a fluxmeter for measuring minute biomagnetism produced by the living body. The multichannel SQUID sensor has a multiplicity of SQUID sensors immersed in a coolant such as liquid nitrogen within a vessel called a Dewar.

With a biosignal measuring apparatus or biomagnetism measuring apparatus having the multichannel SQUID sensor (which may be referred to hereinafter as "fluxmeter" for short), the fluxmeter is placed adjacent a site of interest, e.g. the head, of a patient. The SQUID sensors in the fluxmeter carry out a noninvasive measurement of minute biomagnetism produced by bioelectric currents occurring in the head, and output magnetism detection signals. Based on the magnetism detection signals from the SQUID sensors, a biomagnetism analysis is performed to determine states of the bioelectric current sources, such as locations, orientations and sizes (see Japanese Patent Publication (Unexamined) H7-327943, for example).

With the conventional biomagnetism measuring apparatus, however, it is difficult to remove noise components sufficiently from the magnetism detection signals provided by the SQUID sensors. The biomagnetism to be measured is extremely weak, and inevitably has, mixed thereinto, noise magnetism (which may be called environmental noise) produced from magnetic sources other than the bioelectric current sources. Thus, the magnetism detection signals from the respective SQUID sensors include noise components due to the noise magnetism having mixed thereinto. An accurate analysis of biomagnetism is not assured without sufficiently removing the noise components from the magnetism detection signals.

It is conceivable to use separate magnetic sensors exclusively for detecting noise magnetism alongside the biomagnetism measuring SQUID sensors. That is, it has been proposed to perform a correction process, using noise magnetism detection signals acquired by simultaneously measuring only noise magnetism, to remove noise components from the magnetism detection signals provided the biomagnetism measuring SQUID sensors.

In this case, the noise magnetism detecting magnetic sensors and the biomagnetism measuring SQUID sensors are installed in different positions, and therefore the noise magnetism detection signals acquired through the noise magnetism detecting sensors are not in precise correspondence with the noise components included in the magnetism detection signals of the biomagnetism measuring SQUID sensors. Thus, the noise components included in the magnetism detection signals of the biomagnetism measuring SQUID sensors have to be deduced from the noise magnetism detection signals acquired through the noise magnetism detecting sensors.

However, it is extremely difficult to determine accurately the noise components in spatially different positions partly because noise magnetism presents a complex aspect. As a result, the noise components cannot be removed sufficiently from the magnetism detection signals of the biomagnetism measuring SQUID sensors.

SUMMARY OF THE INVENTION

This invention has been made having regard to the state of the art noted above, and its object is to provide a biosignal measuring method and apparatus for removing noise components sufficiently from detection signals outputted from biosignal measuring sensors.

The above object is fulfilled, according to this invention, by a biosignal measuring apparatus for measuring, with a plurality of sensors, minute biosignals generated from bioelectric current sources in a region of a patient to be diagnosed, the apparatus comprising:

a signal decomposing device for decomposing detection signals provided by the plurality of sensors into a plurality of independent components;

a noise component removing device for determining noise components among the independent components based only on states of the independent components, and removing the noise components;

a signal restoring device for deriving restored detection signals from respective non-noise independent components; and a signal analyzing device for determining an intracerebral activity (location, orientation and strength) corresponding to each independent component of each of the restored detection signals.

When performing a biosignal measurement with the apparatus according to this invention, the plurality of sensors are first set adjacent a region of a patient to be diagnosed. The sensors pick up minute biomagnetism generated from bioelectric current sources, for example. Detection signals (i.e. original detection signals) provided by these sensors are decomposed into a plurality of independent components by the signal decomposing device. Noise components among the independent components are determined and removed by the noise component removing device. Subsequently, the signal restoring device restores the detection signals (restored detection signals) based only on non-noise independent components remaining after the noise components are removed. The restored detection signals are transmitted to the signal analyzing device. The signal analyzing device performs a biosignal analysis based on the restored detection signals, thereby to determine locations and waveforms of the individual biosignals.

The invention uses the ICA (Independent Component Analysis) technique which decomposes each signal into a plurality of signals with a statistically high degree of independence as noted above. The original detection signals (observation signals) provided by the sensors are decomposed into independent components for respective bioelectric current sources and other sources. Then, it is determined whether or not each independent component is a noise component based only on the state of that component. After removing those independent components determined to be noise components, the detection signals are restored from the remaining, non-noise independent components. Thus, without requiring separate magnetic sensors exclusively for detecting noise, restored magnetism detection signals sufficiently stripped of noise components for the purpose of biosignal analysis are obtained, in the form decomposed into components, only from the signals acquired through the biomagnetism measuring sensors. This allows an accurate signal analysis to be performed based on the restored detection signals.

In the apparatus according to this invention, the noise component removing device, preferably, is operable, with reference to a ratio Ma/Mb between a standard deviation Ma of each independent component for a non-examination period within an entire detection signal measuring time, which non-examination period runs from a start of measurement to a point of time when a stimulus is applied to the patient, and a standard deviation Mb for an examination period following the point of time when the stimulus is applied, to determine an independent component with the ratio Ma/Mb equal to or greater than a fixed value to be a noise component, and an independent component with the ratio Ma/Mb less than the fixed value to be a non-noise component.

Non-noise independent components are generated, for example, after a point of time when a stimulus is applied, and therefore grow after that point of time. Conversely, noise components are not directly related to the period after the point of time when the stimulus is applied, and show little variation across the point of time the stimulus is applied. Consequently, the ratio Ma/Mb between standard deviation Ma for the non-examination period and standard deviation Mb for the examination period is small for the independent components that are true signal components, and large for the noise independent components. Whether an independent component is a noise component or not may be determined by monitoring the value of ratio Ma/Mb.

In the apparatus according to this invention, the signal decomposing device, preferably, is operable to determine and average independent components for each event a plurality of times.

When examining a reaction of the brain to a sound, for example, the averaging of the independent components is effective to remove unwanted components such as quantum noise as well as magnetism resembling spike wave generated from the eye muscles and magnetism due to alpha wave steadily generated from the brain.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENT

A preferred embodiment of this invention will be described in detail hereinafter with reference to the drawings.

Figure 1:
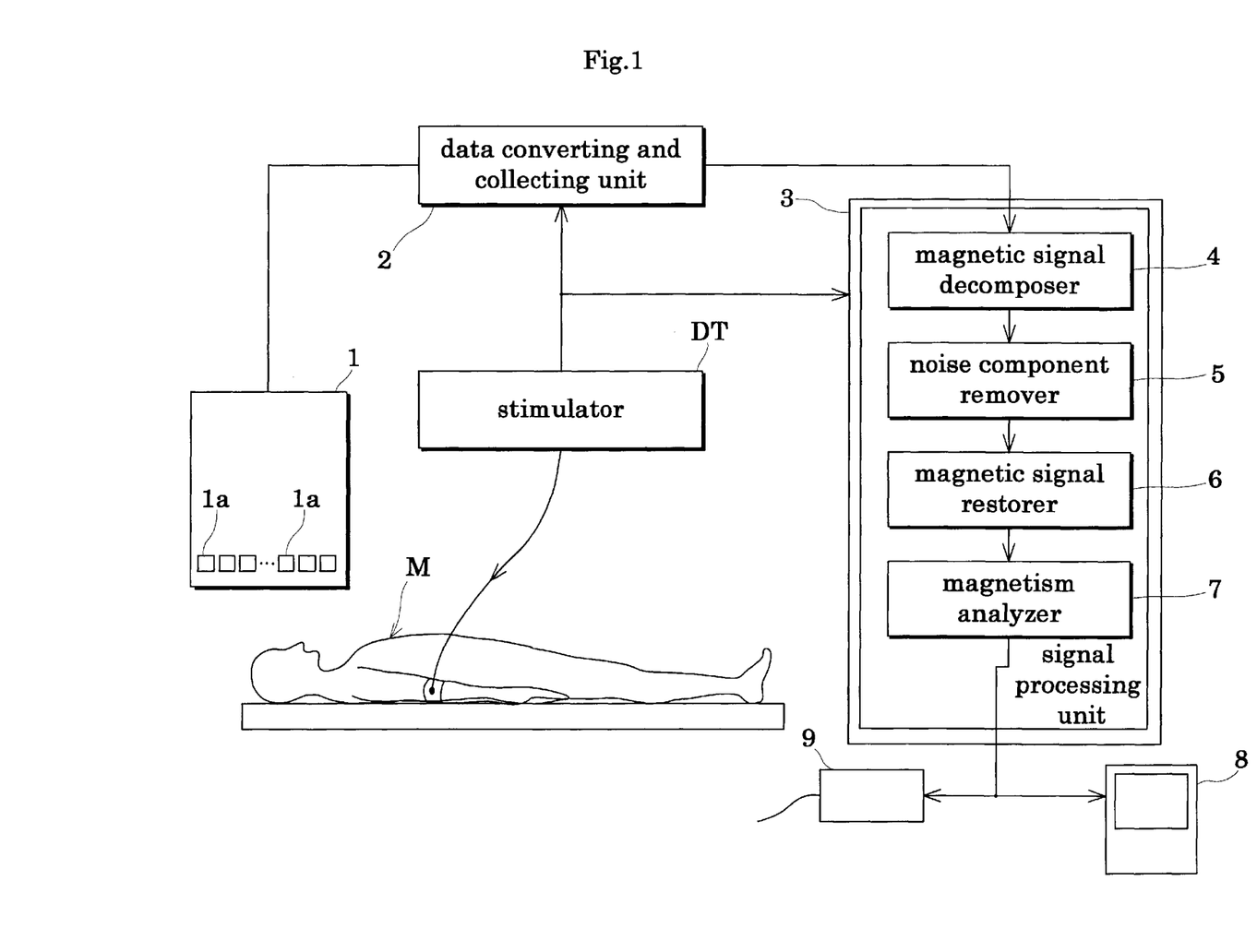
FIG. 1 is a block diagram showing an outline of a biomagnetism measuring apparatus according to this invention.

FIG. 1 is a block diagram showing an outline of a biomagnetism measuring apparatus which is one example of biosignal measuring apparatus according to this invention.

As shown in FIG. 1, this biomagnetism measuring apparatus includes a multichannel SQUID sensor 1 for measuring minute biomagnetism produced by bioelectric current sources in a diagnosed site of an examinee (patient) M, a data converting and collecting unit 2 for appropriately converting and collecting output data (output signals) from the multichannel SQUID sensor 1, and outputting the data as original magnetism detection signals, and a signal processing unit 3 for removing noise components from the original magnetism detection signals received from the data converting and collecting unit 2 and for performing a biomagnetism analysis of the detection signals.

The multichannel SQUID sensor 1 has numerous SQUID sensors 1a suited for measuring minute biomagnetism. The SQUID sensors 1a are arranged in an array of rows and columns and immersed in a coolant such as liquid nitrogen within a vessel called a Dewar.

The multichannel SQUID sensor 1 in this embodiment has SQUID sensors 1a for 128 channels. One biomagnetism measuring time of each channel is 512 msec, for example.

The numerous SQUID sensors 1a correspond to the plurality of sensors in this invention.

The data converting and collecting unit 2 disposed downstream of the multichannel SQUID sensor 1 converts the output signals of the respective SQUID sensors 1a into digital signals, collects the digital signals, and transmits these signals as original magnetism detection signals to the signal processing unit 3. In this embodiment, the original magnetism detection signals are handled as signals in a matrix form having 128 rows and 512 columns.

The signal processing unit 3 is the characterizing component of the biomagnetism measuring apparatus according to this invention. The signal processing unit 3 includes a magnetic signal decomposer 4 for decomposing the original magnetism detection signals into a plurality of independent components, a noise component remover 5 for determining and removing noise components from among the independent components provided by the magnetism signal decomposer 4, based only on the states of the independent components, and a magnetic signal restorer 6 for restoring the original magnetism detection signals from noise-free independent components remaining after the noise component removal, and outputting each restored magnetism detection signal corresponding to a component. The signal processing unit 3 further includes a magnetism analyzer 7 for analyzing biomagnetism based on the restored magnetism detection signals received from the magnetic signal restorer 6. A stimulator DT is provided for stimulating the living body to destroy polarization (dipoles) in the living body and produce bioelectric currents.

The above magnetic signal decomposer 4 corresponds to the signal decomposing device of this invention. The noise component remover 5 corresponds to the noise component removing device. The magnetic signal restorer 6 corresponds to the signal restoring device. The magnetism analyzer 7 corresponds to the signal analyzing device.

The respective components of the signal processing unit 3 will be described in greater detail hereinafter.

The magnetic signal decomposer 4 performs a computation for deriving ICA (Independent Component Analysis) signals X in a matrix form of 128 rows and 512 columns by using the original magnetism detection signals B in the matrix form of 128 rows and 512 columns acquired from a measuring operation and a predetermined ICA (Independent Component Analysis) matrix W in the form of 128 rows and 128 columns.

That is, the magnetic signal decomposer 4 performs a computation X=WB according to the ICA (Independent Component Analysis) technique, to decompose the original magnetism detection signals B into a plurality of independent components corresponding to signal components of bioelectric current sources and other magnetic sources.

The ICA matrix W used herein is probed and determined in advance so that each element of the ICA (Independent Component Analysis) signals X decomposed by the computation WB is independent of the other elements. In this embodiment, the matrix W is determined by regarding the ICA signals X as time series stages with "0" cross-correlation function.

In this embodiment, the magnetic signal decomposer 4 is operable also to determine and average the ICA signals X a plurality of times for each event. The number of times for repetition is selected from the range of several times to several hundred times.

When examining a reaction of the brain to a sound, for example, the averaging of ICA signals X is effective to remove unwanted components such as quantum noise as well as magnetism resembling spike wave generated from the eye muscles and magnetism due to alpha wave steadily generated from the brain.

Conversely, when it is desired to retain magnetism generated from the eye muscles or magnetism due to alpha wave steadily generated from the brain, the averaging may be repeated a reduced number of times or no averaging may be performed.

The noise component remover 5 first determines whether each independent component of the ICA signals X provided by the magnetic signal decomposer 4 is a noise component or not.

In this embodiment, a ratio Ma/Mb is determined, for each row vector of the ICA signals X, between a standard deviation Ma for a non-examination period (e.g. 0 to 200 msec) within the entire measuring time of 512 msec, which runs from a start of measurement to a point of time when the stimulator DT applies a stimulus to the patient, and a standard deviation Mb for an examination period (e.g. 200 to 512 msec) following the point of time when the stimulator DT applies the stimulus. When the ratio is equal to or greater than a fixed value, the independent component corresponding to the row vector is regarded as a noise component. When the ratio is less than the fixed value, the independent component corresponding to the row vector is regarded as a true signal component.

The biomagnetism determining non-noise independent components (true signal components) is generated after the point of time when the stimulator DT applies the stimulus, and therefore the row vector element grows after the point of time the stimulus is applied. Conversely, noise magnetism corresponding to noise components is not directly related to the period after the point of time when the stimulator DT applies the stimulus, and the row vector element shows little variation across the point of time the stimulus is applied. Consequently, the ratio Ma/Mb between standard deviation Ma for the non-examination period and standard deviation Mb for the examination period is small for the independent components that are true signal components, and large for noise independent components. Whether an independent component is a noise component or not may be determined by monitoring the value of ratio Ma/Mb.

That is, the noise component remover 5 removes the components found to be noise components (particularly those noise components called environmental noise). The removal of the noise components is performed by substituting zero for the row vector corresponding to the independent component found to be a noise component. With the noise component removal by the noise component remover 5, the ICA signals X become ICA signals Xa.

The magnetic signal restorer 6 performs a computation for determining restored magnetism detection signals Ba in the matrix form of 128 rows and 512 columns by using the ICA signals Xa provided by the noise component remover 5 and an inverse ICA matrix $W^{-1}$ in the matrix form of 128 rows and 128 columns which is an inverse of the ICA (Independent Component Analysis) matrix W. That is, the magnetic signal restorer 6 performs a computation $W^{-1}Xa$ to derive restored magnetism detection signals Ba (=$W^{-1}Xa$) corresponding to the original magnetism detection signals B from which noise components are removed sufficiently.

The magnetic signal restorer 6 can also restore a magnetism detection signal for each independent signal source. That is, in this case, the restored magnetism detection signals Ba may be obtained by performing the computation $W^-Xa$, using those ICA signals Xa provided by the noise component remover 5 which retain only the row vectors corresponding to the independence components to be restored, with all the other elements replaced by zero.

The magnetism analyzer 7 analyzes biomagnetism based on the restored magnetism detection signals Ba. Specifically, states of bioelectric current sources are determined by deriving a distribution of centers of gravity of the bioelectric current sources from one dipole analysis of the restored magnetism detection signals Ba, or deriving a spatial distribution of the bioelectric current sources from spatial filtering of the restored magnetism detection signals Ba.

The signal processing unit 3 in this embodiment is comprised mainly of a computer and control programs therefor.

Further, the apparatus in this embodiment includes output devices such as a display monitor 8 for displaying results of analyses on the screen thereof, and a printer 9 for printing the results of analyses on sheets. Thus, the positions of centers of gravity or the spatial distribution of the bioelectric current sources provided by the magnetism analyzer 7 may be displayed on the display monitor 8 and/or printed by the printer 9 as necessary.

A biomagnetism measuring operation of the biomagnetism measuring apparatus in this embodiment described in detail hereinbefore will particularly be described with reference to the drawings.

Figure 2:
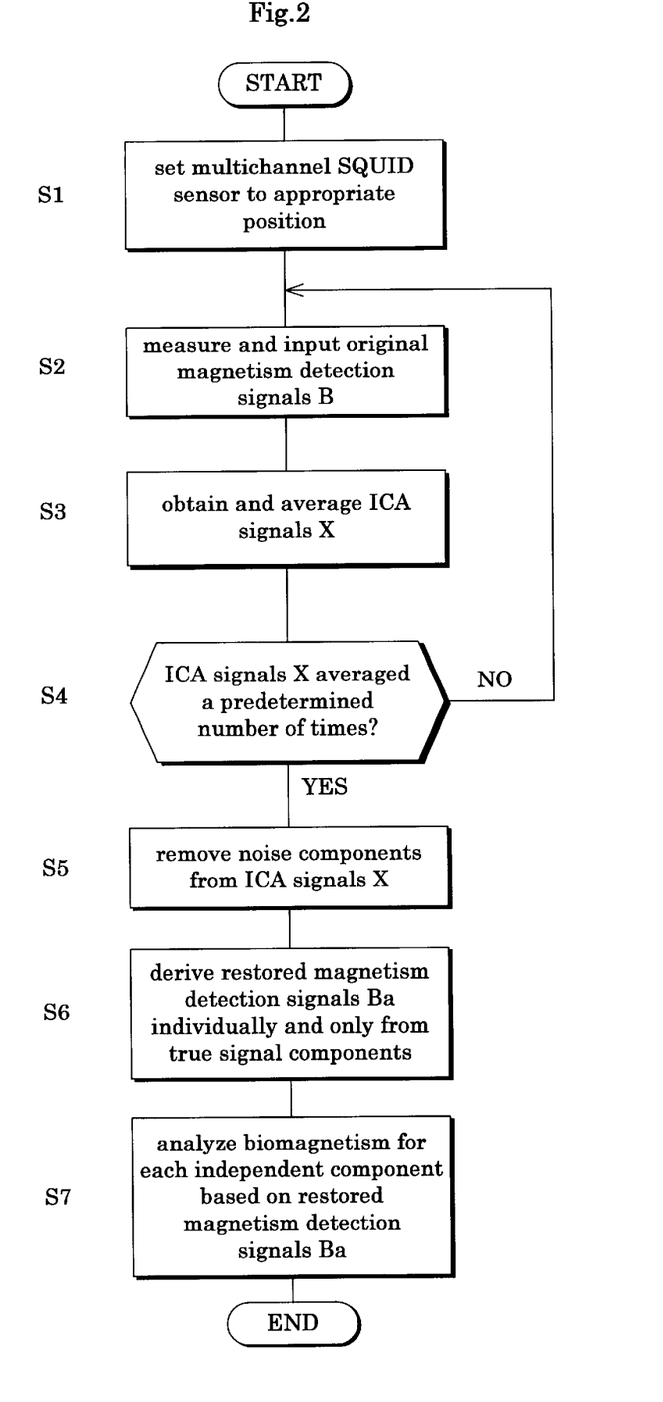
FIG. 2 is a flow chart of a biomagnetism measuring sequence performed by the apparatus according to this invention.
Figure 3:
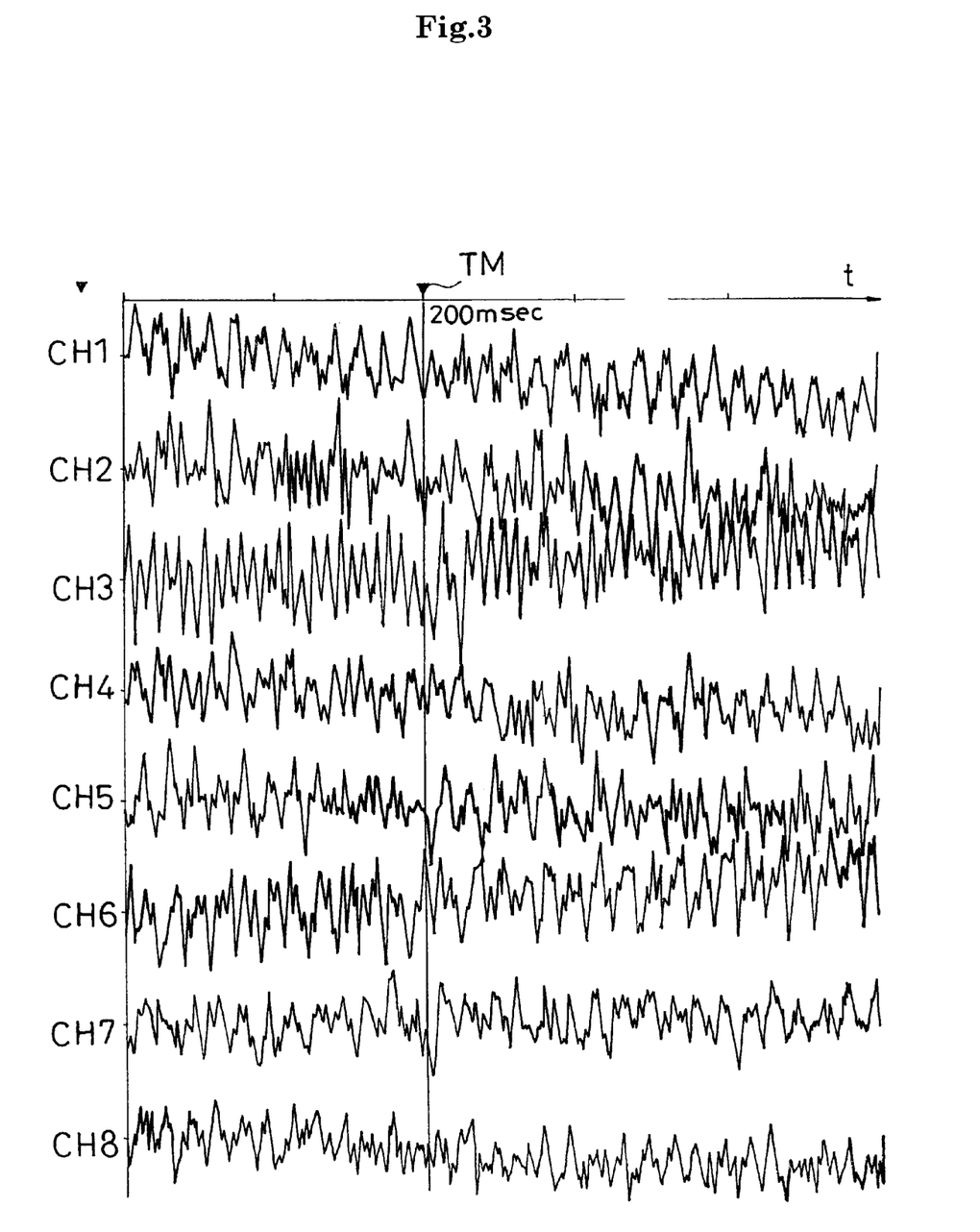
FIG. 3 is a graph showing time-dependent changes of eight channels of original magnetism detection signals.
Figure 4:
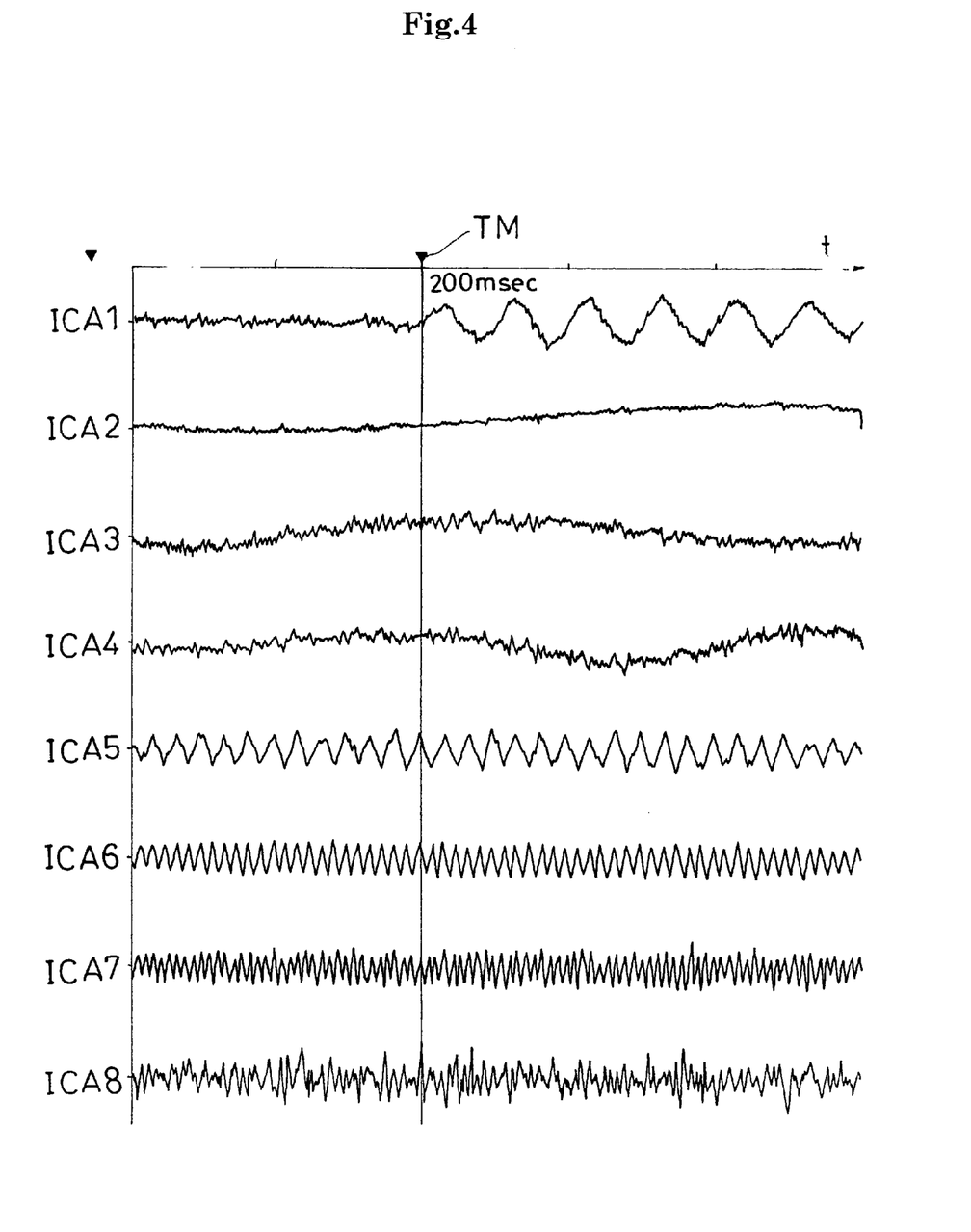
FIG. 4 is a graph showing time-dependent changes of eight independent components of ICA signals.
Figure 5:
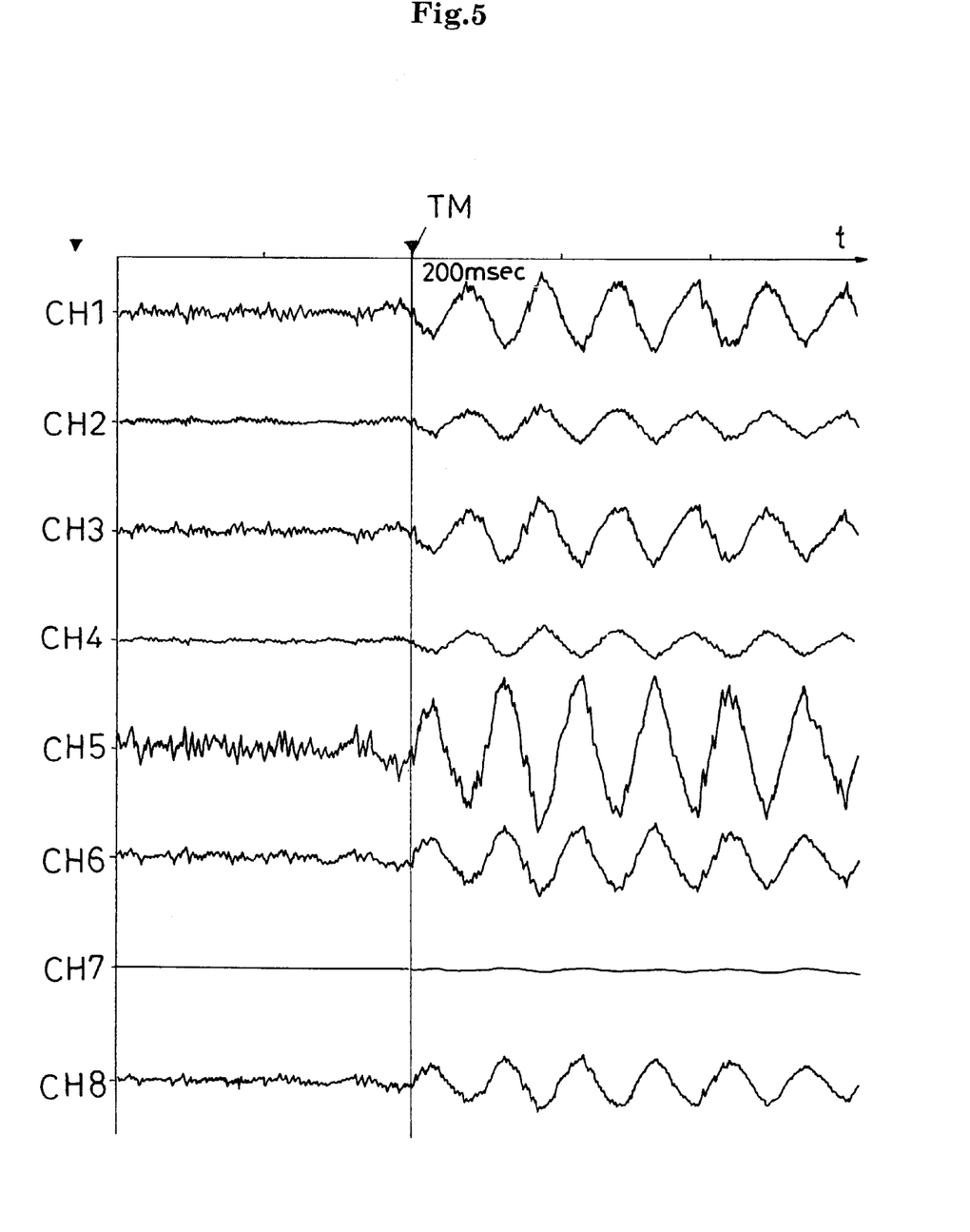
FIG. 5 is a graph showing time-dependent changes of eight independent components of ICA signals.

FIG. 2 is a flow chart of a biomagnetism measuring sequence performed by the apparatus in this embodiment. FIG. 3 is a graph showing time-dependent changes of the original magnetism detection signals. FIG. 4 is a graph showing time-dependent changes of ICA signals X. FIG. 5 is a graph showing time-dependent changes of the restored magnetism detection signals.

In the case described hereinafter, the following models were used as the patient M to facilitate understanding. Current dipoles (electrodes) are arranged as models of bioelectric current sources in a phantom simulating the human head. In place of the stimulus applied to the living body by the stimulator DT, a triangular wave current is applied to the current dipoles at a point of time TM which is 200 msec from a start of measurement.

[Step S1]

The multichannel SQUID sensor 1 is set beside the phantom.

[Step S2]

Upon start of measurement, as shown in FIG. 3, original magnetism detection signals B are inputted to the signal processing unit 3. FIG. 3 is a graph showing time-dependent changes of eight channels CH1–CH8 of original magnetism detection signals B. The triangular wave current is applied to the current dipoles at the point of time TM on time axis t in FIG. 3.

[Step S3]

The magnetic signal decomposer 4 decomposes the original magnetism detection signals B into 128 independent components to obtain ICA signals X, and averages the ICA signals X.

[Step S4]

It is checked whether the ICA signals X have been averaged a predetermined number of times or not. When the predetermined number of times has been reached, the operation proceeds to step S5. Otherwise, the operation returns to step S2.

[Step S5]

The component remover 5 checks whether each independent component of ICA signals X is a noise component or not. The independent components determined to be noise components are removed to obtain ICA signals Xa.

FIG. 4 is a graph showing time-dependent changes of eight independent components ICA1–ICA8 of ICA signals X, which are normalized along the vertical axis. In this case, all but the independent component ICA1 corresponding to the magnetism of the triangular wave current flowing to the current dipoles are determined to be noise components. The independent component ICA2, for example, appears noise magnetism due to geomagnetism, and the independent component ICA5 noise magnetism due to a 60 Hz commercial power supply.

[Step S6]

The magnetic signal restorer 6 derives restored magnetism detection signals Ba. FIG. 5 is a graph showing time-dependent changes of eight channels CH1–CH8 of restored magnetism detection signals Ba. A comparison between the signal waveforms in FIG. 5 and FIG. 3 shows that the S/N ratio is improved by about one digit. It will be appreciated that the removal of the independent components determined at step S5 to be noise components results in the restored magnetism detection signals Ba sufficiently stripped of the noise components.

[Step S7]

Based on the restored magnetism detection signals Ba obtained, the magnetism analyzer 7 performs a biomagnetism analysis to determine a distribution of the centers of gravity of bioelectric current sources or a spatial distribution of the bioelectric current sources. The results of the analysis are outputted by the display monitor 8 and/or printer 9 to complete the measuring operation.

As particularly described above, the biomagnetism measuring apparatus in this embodiment, based on the ICA (Independent Component Analysis) technique, decomposes the original magnetism detection signals into independent components for the respective magnetic sources, and determines whether or not each independent component is a noise component based only on the state of the independent component. The apparatus removes the independent components determined to be noise components, and thereafter restores the magnetism detection signals based on non-noise independent components. Thus, without requiring separate magnetic sensors exclusively for detecting noise magnetism, restored magnetism detection signals sufficiently stripped of noise components for the purpose of biomagnetism analysis are obtained with ease only from the signals acquired with the biomagnetism measuring sensors.

Further, the biomagnetism measuring apparatus according to this invention also removes, by averaging ICA signals X, unwanted components such as noise components generated irregularly and quantum noise.

Figure 6:
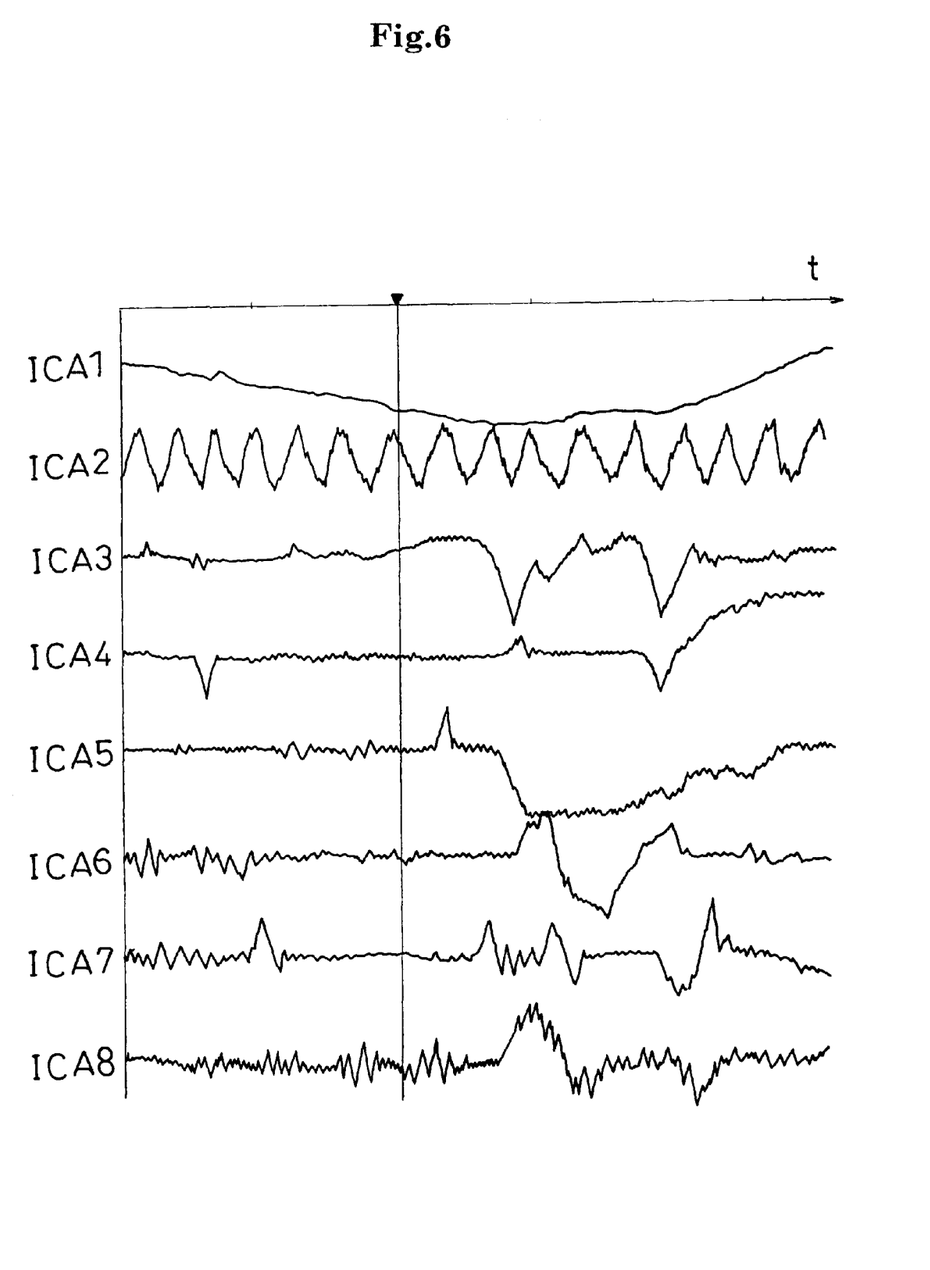
FIG. 6 is a graph showing time-dependent changes of ICA signals derived from original magnetoencephalographic signals.

To illustrate the characteristics of this invention, an example of analyzing a magnetoencephalograph acquired by actually applying a visual stimulus to the patient M will be described with reference to FIG. 6. FIG. 6 is a graph showing time-dependent changes of ICA signals derived from original magnetoencephalographic signals.

Independent component ICA1 is considered noise magnetism due to geomagnetism. Independent component ICA2 is considered noise magnetism due to a 60 Hz commercial power supply. These components are removed as noise components. Here, components ICA3–8 determined to be non-noise independent components are used to derive restored magnetoencephalographic signals therefrom, respectively, for a signal source analysis. An intracerebral activity corresponding to each independent component may be determined in this way.

Figure 7:
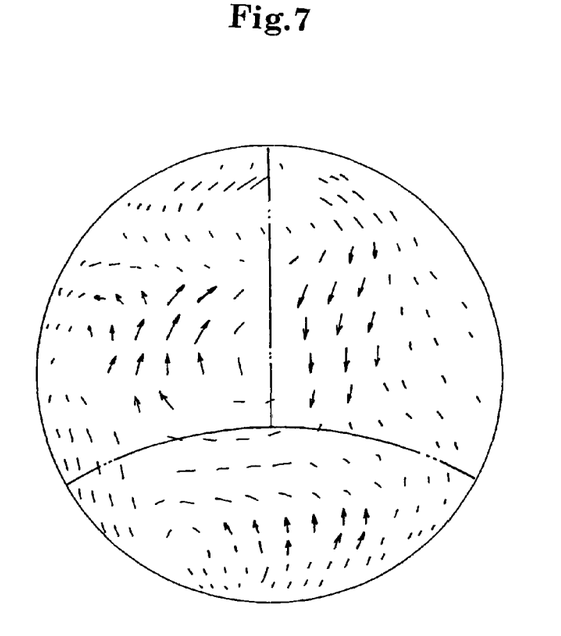
FIG. 7 is a view showing results of a signal source analysis conducted by a spatial filtering of restored magnetoencephalographic signals.

For example, FIG. 7 shows results of a signal source analysis conducted by a spatial filtering of magnetoencephalographic signals restored only from independent component ICA3. This figure shows, with arrows, a distribution of bioelectric currents on an MRI image of the occipital lobe. The length of each arrow corresponds to current strength. The direction of each arrow corresponds to current orientation. Similarly, FIG. 8 shows results of a signal source analysis conducted by a spatial filtering of magnetoencephalographic signals restored only from independent component ICA4.

Figure 8:
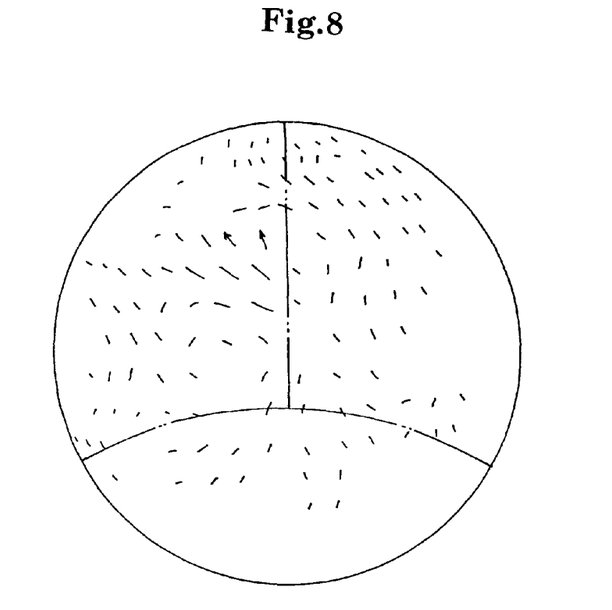
FIG. 8 is a view showing results of a signal source analysis conducted by a spatial filtering of restored magnetoencephalographic signals different from those used in FIG. 7.

The spatial distributions of the signals in FIGS. 7 and 8 are clearly different. It will be seen that each ICA component expresses a signal with a different spatial distribution. This indicates that independent components can separate and clarify magnetoencephalographic signals against a plurality of current sources induced in the human brain by a visual stimulus.

This invention is not limited to the foregoing embodiment, but may be modified as follows:

(1) In the foregoing embodiment, whether the independent components of ICA signals X are noise components or not is determined based on the ratio Ma/Mb between the standard deviation Ma for the non-examination period and the standard deviation Mb for the examination period. In a modified example, whether the independent components of ICA signals X are noise components may be determined based on the signal strengths of the independent components.

For example, the independent components at 1 pT (picoteras) or above are determined to be noise components. In this modification, however, the signal strength of an independent component to be determined is not a normalized value, and has to be converted to a value corresponding to the raw field strength.

(2) In another modified example, the apparatus may determine whether the independent components of ICA signals X are noise components or not based on the frequencies of the independent components.

For example, an FFT may be applied to the ICA signals X to determine the most predominant frequency, and the components at 100 Hz or above may be determined to be noise components.

(3) In a further modified example, the apparatus may determine whether the independent components of ICA signals X are noise components or not based on a combination of two or three of the three noise component determining methods described hereinbefore including the one used in the embodiment.

The foregoing embodiment has been described, taking a biomagnetism measuring apparatus with a magnetoencephalograph for example. The invention produces similar effects when applied to a biosignal measuring apparatus with an electroencephalograph or the like.

The present invention may be embodied in other specific forms without departing from the spirit or essential attributes thereof and, accordingly, reference should be made to the appended claims, rather than to the foregoing specification, as indicating the scope of the invention.

What is claimed is:

1. A biosignal measuring method for measuring, with a plurality of sensors, minute biosignals generated from bioelectric current sources in a region of a patient to be diagnosed, said method comprising:

a signal decomposing step for decomposing detection signals provided by said plurality of sensors into a plurality of independent components, said signal decomposing step being executed to determine and average said independent components for a predetermined number of times;

a noise component-removing step for determining noise components among said independent components based only on states of said independent components, and removing said noise components;

a signal restoring step for deriving restored detection signals from respective non-noise independent components; and a signal-analyzing step for determining an intracerebral activity (location, direction and strength) corresponding to each independent component of each of said restored detection signals, wherein said noise component removing step is executed, with reference to a ratio Ma/Mb between a standard deviation Ma of each independent component for a non-examination period within an entire detection signal measuring time, which non-examination period runs from a start of measurement to a point of time when a stimulus is applied to the patient, and a standard deviation Mb for an examination period following said point of time when said stimulus is applied, to determine an independent component with said ratio Ma/Mb equal to or greater than a fixed value to be a noise component, and an independent component with said ratio Ma/Mb less than said fixed value to be a non-noise component.

2. A biosignal measuring method as defined in claim 1, wherein said signal decomposing step is executed to derive independent component analysis signals X from a computation X=WB, using detection signals B in a matrix form and an independent component analysis matrix W in a predetermined matrix form.

3. A biosignal measuring method as defined in claim 2, wherein said signal restoring step is executed to derive restored detection signals Ba from a computation $Ba=W^{-1}Xa$, using non-noise independent components Xa and an inverse matrix $W^{-1}$ of said independent component analysis matrix W.

4. A biosignal measuring apparatus for measuring, with a plurality of sensors, minute biosignals generated from bioelectric current sources in a region of a patient to be diagnosed, said apparatus comprising:

signal decomposing means for decomposing detection signals provided by said plurality of sensors into a plurality of independent components, said signal decomposing means being operable to determine and average said independent components for each a predetermined number of times;

noise component removing means for determining noise components among said independent components based only on states of said independent components, and removing said noise components;

signal restoring means for deriving restored detection signals from respective non-noise independent components; and signal analyzing means for determining an intracerebral activity (location, direction and strength) corresponding to each independent component of each of said restored detection signals, wherein said noise component removing means is operable, with reference to a ratio Ma/Mb between a standard deviation Ma of each independent component for a non-examination period within an entire detection signal measuring time, which non-examination period is from a start of measurement to a point of time when a stimulus is applied to the patient, and a standard deviation Mb for an examination period following said point of time when said stimulus is applied, to determine an independent component with said ratio Ma/Mb equal to or greater than a fixed value to be a noise component, and an independent component with said ratio Ma/Mb less than said fixed value to be a non-noise component.

5. A biosignal measuring apparatus as defined in claim 4, wherein said signal decomposing means is operable to derive independent component analysis signals X from a computation X=WB, using detection signals B in a matrix form and an independent component analysis matrix W in a predetermined matrix form.

6. A biosignal measuring apparatus as defined in claim 5, wherein said noise component removing means is operable, for each row vector of the independent component analysis signals X, and with reference to said ratio Ma/Mb between said standard deviation Ma of said each independent component for said non-examination period within said entire detection signal measuring time, which said non-examination period runs from said start of measurement to said point of time when said stimulus is applied to the patient, and said standard deviation Mb for said examination period following said point of time when said stimulus is applied, to determine said independent component corresponding to a row vector with said ratio Ma/Mb equal to or greater than said fixed value to be said noise component, and said independent component corresponding to said row vector with said ratio Ma/Mb less than said fixed value to be said non-noise component.

7. A biosignal measuring apparatus as defined in claim 5, wherein said signal decomposing means is operable to determine and average independent component analysis signals X for each event a plurality of times.

8. A biosignal measuring apparatus as defined in claim 7, wherein said signal restoring means is operable to derive restored detection signals Ba from a computation Ba=$W^{-1}$Xa, using non-noise independent components Xa and an inverse matrix $W^{-1}$ of said independent component analysis matrix W.

9. A biosignal measuring apparatus as defined in claim 5, wherein said signal decomposing means is operable to determine and average independent component analysis signals X for each event a plurality of times.

10. A biosignal measuring apparatus as defined in claim 9, wherein said signal restoring means is operable to derive restored detection signals Ba from a computation Ba=$W^{-1}$Xa, using non-noise independent components Xa and an inverse matrix $W^{-1}$ of said independent component analysis matrix W.

11. A biosignal measuring apparatus as defined in claim 5, wherein said signal restoring means is operable to derive restored detection signals Ba from a computation Ba=$W^{-1}$Xa, using non-noise independent components Xa and an inverse matrix $W^{-1}$ of said independent component analysis matrix W.

12. A biosignal measuring apparatus as defined in claim 5, wherein said signal restoring means is operable to derive restored detection signals Ba from a computation Ba=$W^{-1}$Xa, using non-noise independent components Xa and an inverse matrix $W^{-1}$ of said independent component analysis matrix W.

13. A biosignal measuring apparatus as defined in claim 4, wherein said signal decomposing means is operable to determine and average independent component analysis signals X for each event a plurality of times.

14. A biosignal measuring apparatus as defined in claim 13, wherein said signal restoring means is operable to derive restored detection signals Ba from a computation Ba=$W^{-1}$Xa, using non-noise independent components Xa and an inverse matrix $W^{-1}$ of said independent component analysis matrix W.

15. A biosignal measuring apparatus as defined in claim 4, wherein said signal restoring means is operable to derive restored detection signals Ba from a computation Ba=$W^{-1}$Xa, using non-noise independent components Xa and an inverse matrix $W^{-1}$ of said independent component analysis matrix W.

16. A biosignal measuring apparatus as defined in claim 4, wherein said signal restoring means is operable to derive restored detection signals Ba from a computation Ba=$W^{-1}$Xa, using non-noise independent components Xa and an inverse matrix $W^{-1}$ of said independent component analysis matrix W.

17. A biosignal measuring apparatus comprising:
a signal processing unit, said signal processing unit performs the steps of:
  receiving original magnetism detection signals;
  performing biomagnetism analysis on said original magnetism detection signals to obtain independent component analysis signals;
  averaging said independent component analysis signals;
  removing noise components from said received original magnetism detection signals;
  forming restored magnetism detection signals; and
  performing biomagnetism analysis on said restored magnetism detection signals,
  wherein said noise component remover removes said noise components from said independent component analysis signals, and
  wherein for a detection signal measuring time period, said noise component remover determines a ratio Ma/Mb for an independent component, said independent component corresponding to a row vector of said independent component analysis signals, "Ma" being a standard deviation of each independent component of said independent component analysis signals for a non-examination period, said non-examination period being from a start of said detection signal measuring time period to a point of time when a stimulus is applied to a patient, "Mb" being a standard deviation of said each independent component of said independent component analysis signals for an examination period, said examination period being from said point of time when said stimulus is applied to said patient to the end of said detection signal measuring time period.

18. The apparatus of claim 17, further comprising:
a superconducting quantum interference devices sensor, said superconducting quantum interference devices sensor having a plurality of sensors to measure a plurality of biosignals, each sensor of said plurality of sensors measuring biomagnetism, said measured biomagnetism being outputted from said superconducting quantum interference devices sensor as said plurality of biosignals; and
a data converting and collecting unit, said plurality of biosignals from said superconducting quantum interference devices sensor into said data converting and collecting unit, converting said plurality of biosignals into digital signals, said digital signals being outputted from said data converting and collecting unit as said original magnetism detection signals.

19. The apparatus of claim 18, further comprising:
a stimulator, said stimulator destroying polarization and producing bioelectric currents, said bioelectric currents being said plurality of biosignals.

20. The apparatus of claim 18, further comprising:
a display and a printer, said display displaying results of analysis, said printer printing results of said analysis.

21. The apparatus of claim 17, wherein said signal processing unit including a magnetic signal decomposer, a noise component remover, a magnetic signal restorer, and a magnetism analyzer.

22. The apparatus of claim 21, wherein said magnetic signal decomposer performs said biomagnetism analysis.

23. The apparatus of claim 22, wherein said biomagnetism analysis is X=WB, "X" being said independent component analysis signals, "W" being an independent component analysis matrix, and "B" being said original magnetism detection signals.

24. The apparatus of claim 23, wherein said magnetic signal decomposer performs said biomagnetism analysis a plurality of times to perform said step of averaging said independent component analysis signals.

25. The apparatus of claim 24, wherein said step of averaging said independent component analysis signals includes averaging said independent component analysis signals a predetermined number of times.

26. The apparatus of claim 21, wherein said magnetism analyzer uses said restored magnetism detection signals to perform said biomagnetism analysis.

27. The apparatus of claim 26, wherein said biomagnetism analysis is performed by determining states of bioelectric current sources, said states of bioelectric current sources are determined by deriving a distribution of center of gravity of the bioelectric current sources from one dipole analysis of said restored magnetism detection signals.

28. The apparatus of claim 26, wherein said biomagnetism analysis is performed by deriving a spatial distribution of bioelectric current sources from spatial filtering of said restored magnetism detection signals.

29. The apparatus of claim 26, wherein said biomagnetism analysis determines an intracerebral activity (location, direction and strength) corresponding to each independent component of each of said restored detection signals.

30. The apparatus of claim 17, wherein said independent component is not regarded as said noise component when said independent component has said ratio Ma/Mb less than a fixed value.

31. The apparatus of claim 17, wherein said independent component is regarded as said noise component when said independent component has said ratio Ma/Mb equal to or greater than a fixed value.

32. The apparatus of claim 31, wherein, said restored magnetism detection signals is said original magnetism detection signals with said noise components removed, said noise components being removed by substituting zero for the row corresponding to said independent component found to be said noise component.

33. The apparatus of claim 17, wherein an FFT is applied to said independent component analysis signals to determine a most predominant frequency, the components at 100 Hz or higher being said noise components.

34. The apparatus of claim 17, wherein said magnetic signal restorer generates said restored magnetism detection signals, said restored magnetism detection signals being said original magnetism detection signals with said noise components removed.

35. The apparatus of claim 34, wherein said restored magnetism detection signals are generated using a computation Ba=$W^{-1}$Xa, "Ba" being said restored magnetism detection signals, "$W^{-1}$" being an inverse matrix of said independent component analysis matrix "W", and "Xa" being said independent component analysis signals without said noise components.

* * * * *